United States Patent
Linhardt et al.

(10) Patent No.: US 6,376,662 B1
(45) Date of Patent: Apr. 23, 2002

(54) METHOD FOR SYNTHESIZING C-GLYCOSIDES OF ULOSONIC ACIDS

(75) Inventors: Robert J. Linhardt, Iowa City, IA (US); Iontcho R. Vlahov, Newark, DE (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/142,937

(22) PCT Filed: Jan. 16, 1998

(86) PCT No.: PCT/JP98/00129

§ 371 Date: Nov. 17, 1998

§ 102(e) Date: Nov. 17, 1998

(87) PCT Pub. No.: WO98/31696

PCT Pub. Date: Jul. 23, 1998

Related U.S. Application Data (60) Provisional application No. 60/034,953, filed on Jan. 17, 1997, provisional application No. 60/035,969, filed on Jan. 21, 1997, and provisional application No. 60/035,986, filed on Jan. 23, 1997.

(51) Int. Cl.$^7$ .............................. C07H 7/04; C07H 7/06; C07H 1/00; C07H 7/033
(52) U.S. Cl. ...................... 536/29.2; 549/356; 549/429; 549/563
(58) Field of Search .............................. 536/1.11, 29.2; 549/356, 429, 563

(56) References Cited

PUBLICATIONS

Luthman et al. Synthesis of C–glycosides of 3–deoxy–D–manno–2–octulosonic acid. Stereoselectivity in an enolate reaction. J. Org. Chem. 52 (17), 3777–3784. (Aug./1987).*

Nagy et al. The chemical–enzymatic synthesis of a carbon glycoside of N–acetyl neuraminic acid. Tetrahedron Lett. 32 (32), 3953–3956. (Aug./1991).*

Mazeas et al. A highly stereospecific synthesis of 1,2–trans–C–glycosides via glycosyl samarium (III) compounds. Angew. Chem. Int. Ed. Eng. 34(8), 909–912. (1995). No month.*

Hung et al. Samarium diiodide mediated coupling of glycosyl phosphates with carbon radical or anion acceptors–Synthesis of C–glycosides. Angew. Chem.Int. Ed. Eng. 35 (22), 2671–2674. (1996). No month.*

Jarreton et al. The stereospecific synthesis of methyl α–C–mannobioside: a potential inhibitor of M. Tuberculosis binding to human macrophages. Chem. Commun. 14, 1661–1662. (Jul./1996).*

Vlahov et al. Diastereocontrolled synthesis of carbon glycosides of N–acetylneuraminic acid via glycosyl samarium (III) intermediates. J. Am. Chem. Soc. 119, 1480–1481. (Feb./1997).*

Zeng et al. Chemical Abstracts vol. 114, No. 10, abstract No. 93940. (Mar./1991). Abstract only.*

Zeng et al. Chemical Abstracts vol. 110, No. 16, abstract No. 146509. (Apr./1989). Abstract only.*

Brzyska, W. Chemical Abstracts vol. 86, No. 26, abstract No. 199131. (Jun./1977). Abstract only.*

\* cited by examiner

*Primary Examiner*—Michael P Woodward
*Assistant Examiner*—Marjorie A. Moran
(74) *Attorney, Agent, or Firm*—Birch, Stewart, Kolasch & Birch, LLP (57) ABSTRACT

A method for synthesizing C-glycosides of ulosonic acids such as Neu5Ac, by which diastereocontrolled synthesis of α-C-glycosides of ulosonic acids is attained is disclosed. In the method of the present invention, an ulosonic acid sulfone or phosphite is reacted with an aldehyde or ketone compound in the presence of a lanthanide metal halide.

17 Claims, 4 Drawing Sheets

METHOD FOR SYNTHESIZING C-GLYCOSIDES OF ULOSONIC ACIDS

This application is the national phase under 35 U.S.C. §371 of prior PCT International Application No. PCT/JP98/00129 which has an International filing date of Jan. 16, 1998 which designated the United States of America, the entire contents of which are hereby incorporated by reference. This application claims the benefit of provisional applications No. 60/034,953, filed Jan. 17, 1997, Ser. No. 60/035,969, filed Jan. 21, 1997, and Ser. No. 60/035,986, filed Jan. 23, 1997.

TECHNICAL FIELD

The present invention relates to a method for synthesizing C-glycosides of ulosonic acids, as well as intermediates thereof and particular C-glycosides prepared by the method.

BACKGROUND ART

α-O-glycosides of N-acetylneuraminic acid (Neu5Ac, 1, Scheme 1) are often found terminating the oligosaccharide component of cell-surface glycoproteins and glycolipids. Neu5Ac is involved in a number of important biological events: intercellular interactions such as adhesion, aggregation and agglutination; masking of antigenic oligosaccharides and suppressing undesired immune reactions (antirecognition phenomena); influencing the cell membrane permeability for permeability for ions, amino acids and proteins; and protection of glycoproteins against proteolysis[1]. Terminal Neu5Ac is an attachment site of pathogens to the cells and often catabolic and inflammatory processes are initiated on the removal of this carbohydrate group[2]. In general the "right" life time of a cell is a reflection of a delicate balance between the introduction and removal of terminal Neu5Ac or other sialic acids.

The glycosidic bond of Neu5Ac is cleaved in vivo by hydrolase type enzymes, called neuraminidases[3]. Therefore, designing nonhydrolyzable analogs of Neu5Ac-α-O-glycosides is an attractive approach to control, at the molecular level, events of crucial importance to glycobiology and immunology. The replacement of the interglycosidic oxygen atom by a methylene group, for example, generates a class of hydrolytically and metabolically inert isosteres, the Neu5Ac C-glycosides. Despite several elegant methods for direct carbon-carbon (C—C) bond formation at the anomeric center in aldoses and ketoses[4], no major advances have been reported in the synthesis of Neu5Ac C-glycosides[5]. The major problem confounding their synthesis is the requirement that the C—C bond being formed results in a quaternary C-atom.

DISCLOSURE OF THE INVENTION

Accordingly, an object of the present invention is to provide a method for synthesizing C-glycosides of ulosonic acids such as Neu5Ac, by which diastereocontrolled synthesis of α-C-glycosides of ulosonic acids is attained. Another object of the present invention is to provide intermediates of the novel method, and to provide novel C-glycosides of particular ulosonic acids, which are synthesized by the novel method.

The present inventors intensively studied to discover that diastereocontrolled synthesis of α-C-glycosides of ulosonic acids is attained by carrying out the reaction between ulosonic acid sulfone or phosphite with an aldehyde or ketone compound in the presence of a lanthanide metal halide such as $SmI_2$, thereby completing the present invention.

That is, the present invention provides a method for synthesizing C-glycosides of ulosonic acids comprising the step of reacting an ulosonic acid sulfone or phosphite with an aldehyde or ketone compound in the presence of a lanthanide metal halide.

Preferably, the lanthanide metal halide of the invention is a halide of samarium (II).

The present invention also provides a method for synthesizing C-glycosides of carbohydrates containing a quaternary carbon comprising the step of reacting said carbohydrate with an aldehyde or ketone compound in the presence of a lanthanide metal halide.

The present invention still also provides a method for synthesizing C-glycosides of neuraminic acids or sialic acids comprising the step of reacting the protected neuraminic acid or sialic acid sulfone or phosphite with an aldehyde or ketone compound in the presence of a lanthanide metal halide.

The present invention still also provides a method for synthesizing C-glycosides of KDO comprising the step of reacting the protected KDO sulfone or phosphite with an aldehyde or ketone compound in the presence of a lanthanide metal halide.

The present invention still also provides a method for synthesizing C-glycosides of KDN comprising the step of reacting the protected KDN sulfone or phosphite with an aldehyde or ketone compound in the presence of a lanthanide metal halide.

The present invention still also provides a samarium III adduct of ulsonic acids. The present invention still further provides a samarium III adduct of ulsonic acids.

The present invention still further provides a samarium III adduct of carbohydrates containing a quaternary carbon. The present invention still further provides a samarium III adduct of neuraminic acids or sialic acids. The present invention still further provides a samarium III adduct of 3-deoxy-D-manno-octulosonic acid. The present invention still further provides a samarium III adduct of 2-keto-3-deoxy-D-glycero-d-galactonononanoic acid.

The present invention still further provides C-disaccharide having the structure, methyl 5-acetamido-4,7,8,9-tetra-O-acetyl-2,6-anhydro-3,5-dideoxy-2-C-{(S)-hydroxy-[3-(methyl-2,4,6-tri-O-benzyl-3-deoxy-α-D-galactopyranosidyl)]-methyl}-D-erythro-L-manno-nonanate. The present invention still further provides C-glycoside having the structure, Methyl 5-acetamido-4,7,8,9-tetra-O-acetyl-2,6-anhydro-3,5-dideoxy-2-C-{hydroxy-4-(tert-butylcyclohexyl)]-D-erythro-L-manno-nonanate.

By the present invention, diastereocontrolled synthesis of α-C-glycosides of ulosonic acids is first attained, and novel intermediates and C-glycosides of ulosonic acids were provided.

BEST MODE FOR CARRYING OUT THE INVENTION

As mentioned above, in the method of the present invention, an ulosonic acid sulfone or an ulosonic acid phosphite is reacted with an aldehyde or ketone compound in the presence of a lanthanide metal halide.

As the lanthanide metal halide, halides (iodides, bromides and chlorides) of lanthanide metals may be employed. As the lanthanide metal, samarium, ytterbium and europium are preferred, and samarium is best preferred.

The reactants which react with the lanthanide metal halides are ulosonic acids such as neuraminic acids and sialic acids. Further, other carbohydrates bearing a quaternary carbon at the anomeric position (ketoses) may also be employed as the reactant to be reacted with the lanthanide metal halide. That is, the process of the present invention is directed to the process for synthesizing C-glycosides of ulosonic acids including neuraminic acids and sialic acids. The process may also be applied to the synthesis of C-glycosides carbohydrates containing a quaternary carbon, such as C-glycosides of 3-deoxy-D-manno-octulosonic acid (KDO) and C-glycosides of 2-keto-3-deoxy-D-glycero-d-galactonononanoic acid (KDN).

When the lanthanide metal halide is reacted with neuraminic acid or sialic acid derivatives, the reactant may be represented by the following formula [I]:

[I]

In formula [I], $R^1$ may be aryl sulfone, heteroaromatic sulfone or dialkyl phosphite groups. Specific examples of $R^1$ include pyridyl sulfonyl, phenyl sulfonyl, imidazole sulfonyl, diethylphosphityl and dibenzyl phosphityl groups.

In formula [I], each $R^2$ may be the same or different, and may be any group or atom which does not hinder the reaction, such as acyloxy groups such as those containing straight or branched alkyl groups, especially $C_1$–$C_6$ alkyl groups, benzyloxy groups, allyloxy groups, isopropylidene dioxy groups, cyclohexylidene dioxy groups, silyloxy groups or N-amide groups. Each of these groups may contain one or more, usually 1 to 5 substituents such as methyl, methoxy, benzyloxy, trichloroethoxy and trialkylsilyloxy groups. The most preferred $R^2$ is acyloxy or alkyloxy.

In formula [I], $R^3$ is not restricted at all and may be any group or atom which does not hinder the reaction. For example, $R^3$ may be straight or branched alkyloxy groups especially $C_1$–$C_6$ alkyloxy groups, cyclic alkyloxy groups, arylmethyloxy groups, arylamine groups, alkylamine groups or another carbohydrate moiety. $R^3$ may be substituted with the substituents, usually with 1 to 5 substituents, mentioned above for $R^2$.

In formula [I], X may be oxygen, alkylamine or arylamine, and methylene or substituted methylene.

Equivalents of the skeleton of the structure represented by the formula [I] may include those represented by the following formulae. The meanings of the substituents in the following formulae are as described above.

Formulae

The counterpart reactant which is reacted with the above-mentioned ulosonic acids, carbohydrates containing a quaternary carbon, neuraminic acids or sialic acids, is not restricted at all and any organic compounds having an aldehyde group or ketone group may be employed. When the C-glycosides to be produced is a disaccharide, the preferred counterpart reactant may be represented by the following formula [II]:

[II]

In formula [II], $R^4$ may be any group which does not hinder the reaction. The explanation about $R^3$ in formula [I] may also be applied to $R^4$.

In formula [II], $R^5$ may be the same or different, and may be any group which does not hinder the reaction. The explanation about $R^2$ in formula [I] may also be applied to $R^5$. However, benzyloxy group is also preferred in addition to acyloxy.

In formula [II], $R^6$ may be hydrogen, alkyl group or aryl group.

In formula [II], X may be oxygen, alkylamine or arylamine, and methylene or substituted methylene.

In formula [II], n=0 or 1.

Equivalents of the skeleton of the structure represented by the formula [II] may include those represented by the following formulae. The meanings of the substituents in the following formulae are as described above.

Un less otherwise specified, among any of the above-mentioned groups or substituent groups, in those which is alkyl or which may contain alkyl moiety, the number of carbon atoms may preferably be 1–6. Among any of the above-mentioned groups or substituent groups, in those which is aryl or which may contain aryl moiety, the aryl group may preferably be phenyl, naphthyl, biphenyl, anthryl or phenanthryl. The alkyl group or alkyl moiety and the aryl group or aryl moiety may contain one or more, usually 1 to 5 substituent(s) described for $R^2$.

As the solvent used in the reaction, not only THF, but also other aprotic solvents, such as ethers, halogenated hydrocarbons and tertiary amides such as hexamethylphosphorous triamide (HMDA) and 1,3-dimethyl-3,4,5,6-tetrahydro-2(1H)pyrimidinone (DMPU), may be employed.

The reaction may be carried out at a temperature between −40 to 25° C., preferably 20° C. The concentration of the reactant 8 (in scheme 2) or any equivalent thereof mentioned above may be from neat to 0.01 M, preferably neat. The concentration of the solution of $SmI_2$ or equivalent thereof may be 0.1 M to 0.001 M, preferably 0.1 M. The concentration of the reactant 9 (in scheme 2) or any equivalent thereof mentioned above may be from neat to 0.01 M, preferably neat. The mixing ratio of reactant 8 (or equivalent thereof):reactant 9 (or quivalent thereof):lanthanide metal halide may preferably be 1:(0.2–10):(0.5–20), more preferably 1:(0.5–5):(1–10), still more preferably 1:(1–2):(2–4) in terms of molar equivalence. The reaction time may be 1 min. to 1 hr, preferably 30 min.

As an example, diastereocontrolled synthesis of carbon glycosides of N-acetylneuraminic acid via glycosyl samarium (III) intermediates will now be described in more detail referring to Scheme 1 and Scheme 2.

Scheme 1

This approach is tolerant of a wide variety of protecting groups. The reducing potential of $SmI_2$ is exploited through the in situ generation of an N-acetylneuraminyl samarium (III) species and its coupling to carbonyl compounds under Barbier conditions[6].

In model studies that led to this method, the $SmI_2$-promoted generation of the anomeric capto-dative free radical 3 was attempted, employing an ester tethered Neu5Ac-sulfone 2[7] (Scheme 1). It was anticipated that 3 would collapse into a mixture of C-glycosides by cyclization through an exo and/or endo-modet. Surprisingly, instead of the anticipated cyclic C-glycosides (5 and/or 6), the 2-deoxy compound 7[9] was isolated in excellent yield and stereoselectivity. No trace of the C-2-pimer having an equatorial carboxy function was observed. This exceptional stereoselectivity suggested an intermediate second electron transfer providing the organosamarium(III) derivative 4, in which the bulky $I_2Sm(III)$-substituent adopts the more thermodynamically stable equatorial position.

A diastereocontrolled synthesis of α-linked C-disaccharides was designed using this C-2-samariated Neu5Ac derivative as a $C_9$-nucleophile to react with a C-formyl sugar (a $C_7$-electrophile) (Scheme 2). The proposed $C_9$-nucleophile precursor 8 was obtained in four steps from Neu5Ac as previously described.[7] A 2-pyridyl sulfone, similar to that suggested by Mazeas et al,[8] replaced the phenyl sulfone moiety, decreasing the LUMO-energy level of the $SO_2Ar$, facilitating one electron-transfer and homolytic fragmentation to the intermediate free radical 3. The $C_7$-electrophile 9 was prepared in seven steps from methyl α-D-galactopyranoside as described by Schmidt et al.[10]

Treatment of a neat mixture of sulfone 8 and aldehyde 9 (1.5 equivalent) in inert atmosphere with 3.1 equivalents of freshly prepared 0.1M $SmI_2$ solution in THF at 20° C. gave a nearly instantaneous conversion to the C-disacharide 10 in excellent yield.

Addition of the aldehyde immediately after the SmI$_2$ solution does not lead to a condensation with 8 clearly demonstrating the Barbier conditions of the reaction. Under these conditions, only protonation (presumably from THF) of the intermediate organosamarium(III) species was observed.

Figure 1:
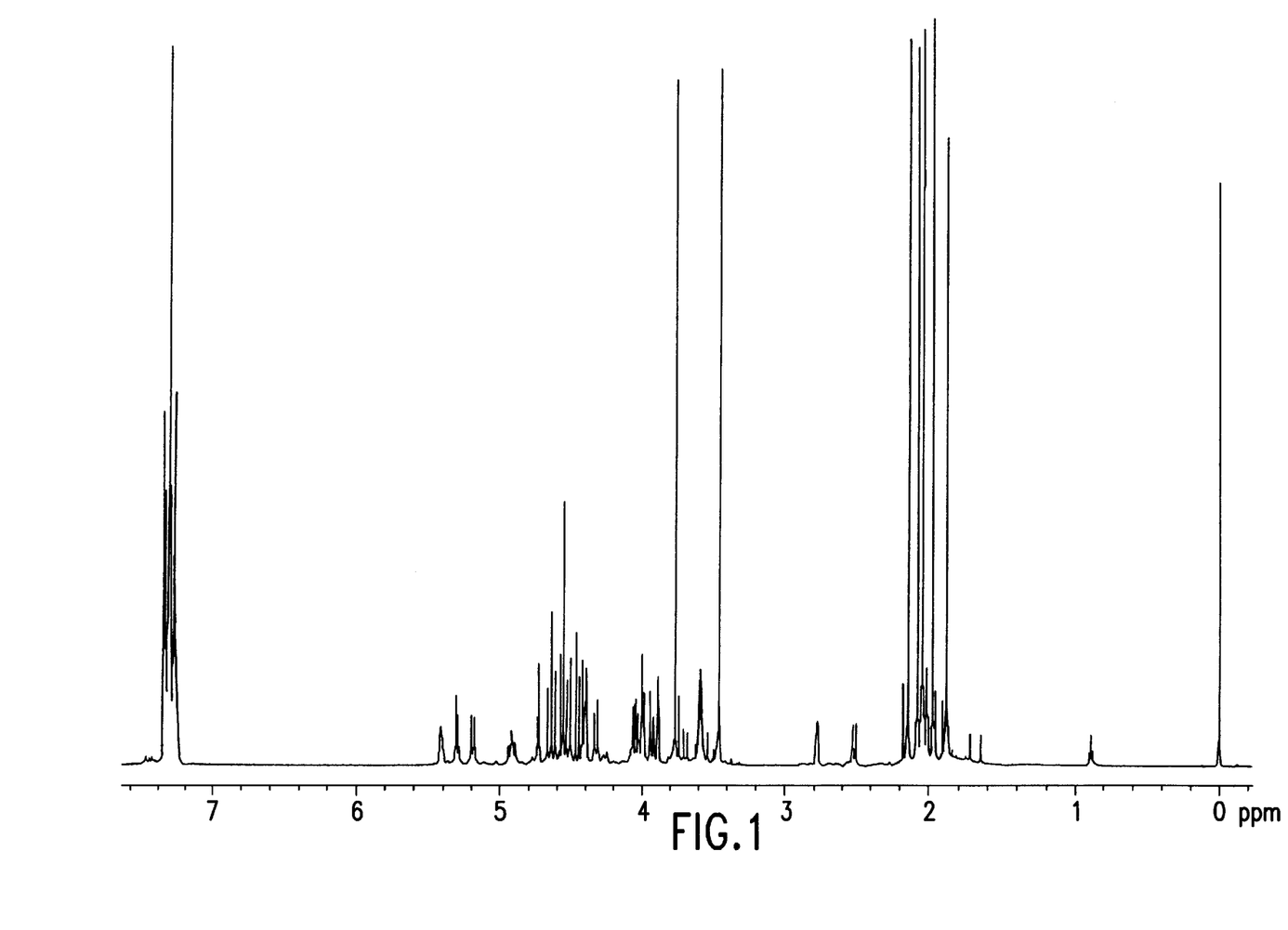
FIG. 1 shows $^1$H-NMR spectrum of methyl 5-acetamido-4,7,8,9-tetra-O-acetyl-2,6-anhydro-3,5-dideoxy-2-C-{(S)-hydroxy-[3-(methyl 2,4,6-tri-O-benzyl-3-deoxy-α-D-galactopyranosidyl)]-methyl}-D-erythro-L-manno-nonanate.
Figure 2:
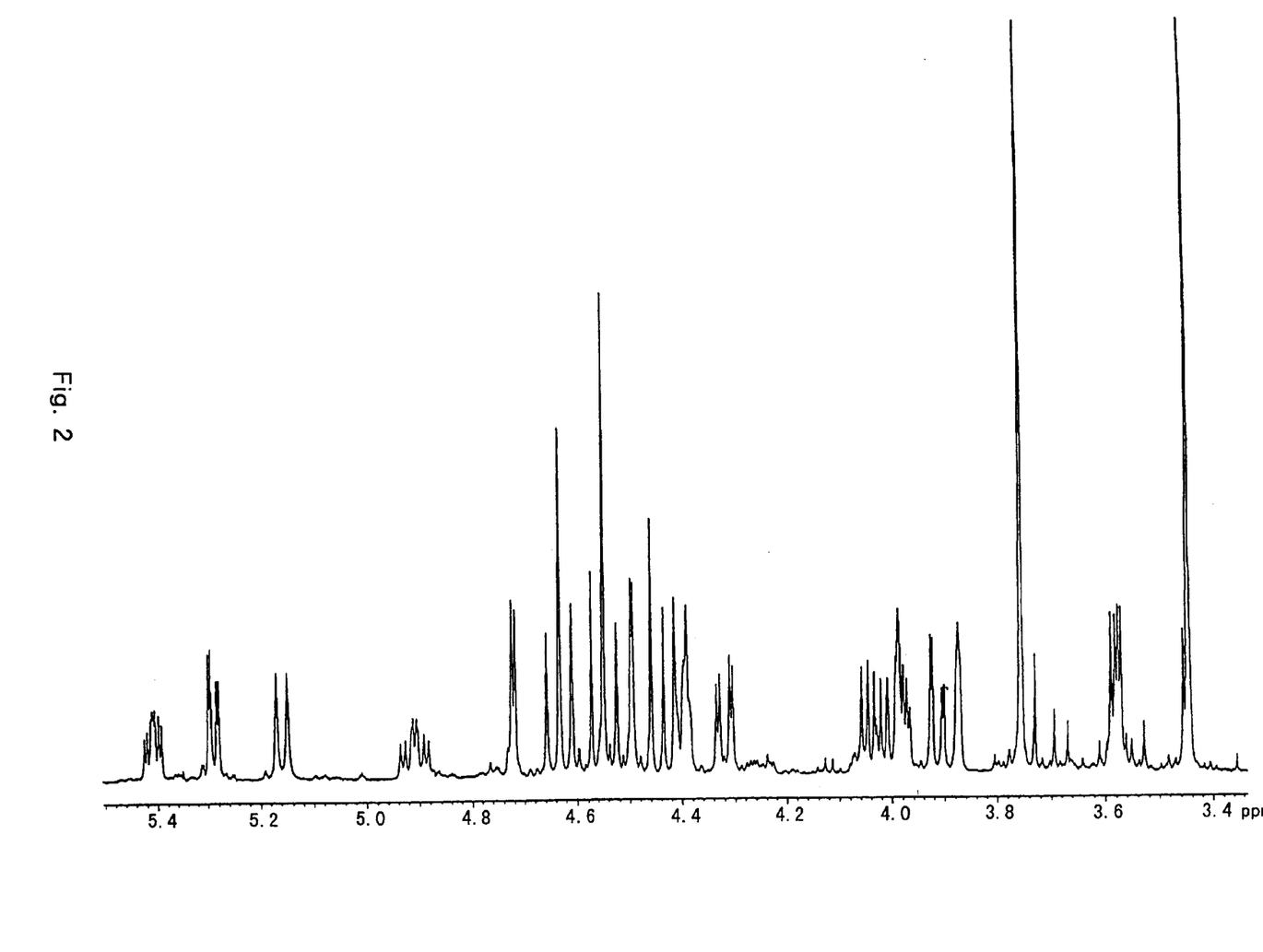
FIG. 2 shows a selected portion of the $^1$H-NMR spectrum of methyl 5-acetamido-4,7,8,9-tetra-O-acetyl-2,6-anhydro-3,5-dideoxy-2-C-{(S)-hydroxy-[3-(methyl 2,4,6-tri-O-benzyl-3-deoxy-α-D-galactopyranosidyl)]-methyl}-D-erythro-L-manno-nonanate.
Figure 3:
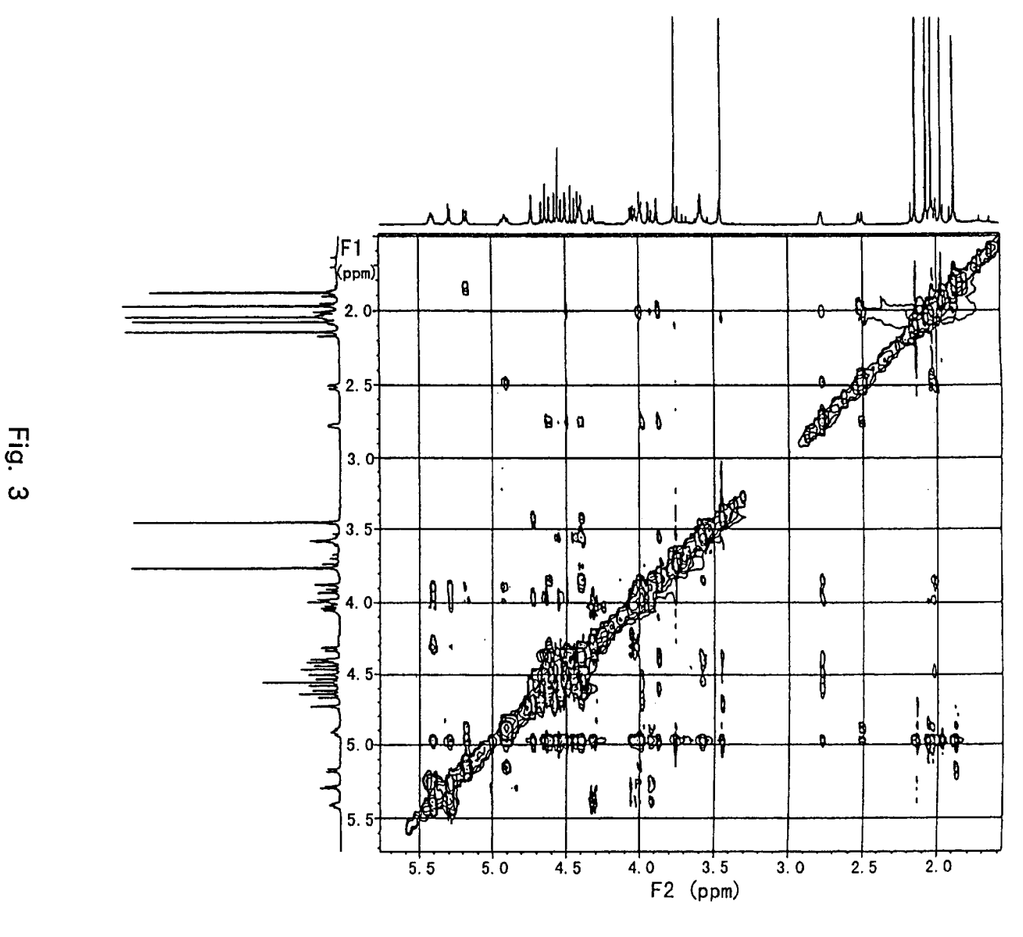
FIG. 3 shows a selected portion of the $^1$H-$^1$H ROESY ($\tau_m$=100 ms) spectrum of methyl 5-acetamido-4,7,8,9-tetra- O-acetyl-2,6-anhydro-3,5-dideoxy-2-C-{(S)-hydroxy-[3-(methyl 2,4,6-tri-O-benzyl-3-deoxy-α-D-galactopyranosidyl)]-methyl}-D-erythro-L-manno-nonanate.
Figure 4:
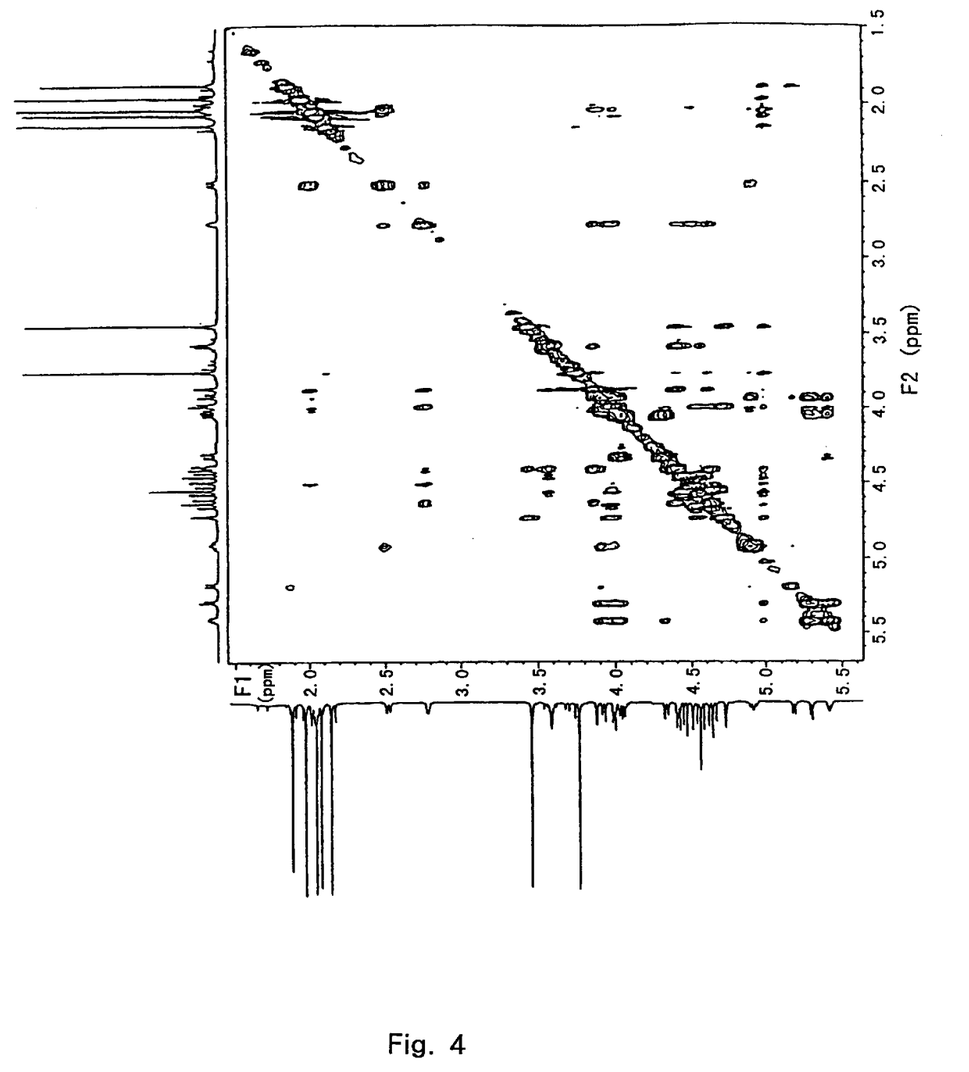
FIG. 4 shows a selected portion of the $^1H$-$^1H$ ROESY ($\tau_m$=700 ms) spectrum of methyl 5-acetamido-4,7,8,9-tetra-O-acetyl-2,6-anhydro-3,5-dideoxy-2-C-{(S)-hydroxy-[3-(methyl 2,4,6-tri-O-benzyl-3-deoxy-α-D-galactopyranosidyl)]-methyl}-D-erythro-L-manno-nonanate.

The structural assignment of 10 was based on 1D and 2D $^1$H-NMR. The formation of the α-anomer was confirmed using empirical rules for determining of the anomeric configuration of Neu5Ac glycosides[12]. The chemical shift of H-4' (4.90 ppm), the $J_{7',8'}$-value (7.7 Hz) and the Δδ/H-9'$_A$–H-9'$_B$/-value (0.26 ppm) clearly indicated the α-configuration of the Neu5Ac residue in 10. The $^1$H-$^1$H ROESY spectra ($τ_m$=700 ms or 100 ms) showed negative NOEs between H-4', H-6' and the protons of the methyl ester group and between H-3'$_{ax}$, H-3'$_{eq}$ and H-3, confirming the α-configuration. Same spectra were used for indirect assignment of the stereochemistry at the newly formed hydroxymethylene bridge. The lack of any NOE between H-4 and H-3'$_{eq}$ indicated a restricted mobility around the both interglycosidic bonds and the negative cross peaks between the proton at the bridging carbon atom and the both C-6 protons of the galacto moiety showed that they are spatially close.

The observed diastereoselectivity of the reaction could be rationalized based on the Felkin-Anh model[13] for predicting the stereochemical outcome of a kinetically controlled addition of a nucleophile to a chiral aldehyde (Scheme 2, A). The bulkiest ligand a to the carbonyl group in 9 is the C-2 atom containing an equatorial benzyloxy group and attached to the C-1 atom bearing an axial α-OMe glycosidic substituent. This ligand has a perpendicular relationship to the plane of the carbonyl group and is anticlinal to the Bürgi-Dunitz trajectory[14] of the incoming nucleophile. Only traces of other diastereomers (<1% based on $^1$H-NMR) were observed after silica gel separation of product 10 and unreacted aldehyde 9.

The coupling of a ketone with 8 was also investigated to establish the scope of this reaction. An excellent yield of C-glycoside 11 was obtained (Scheme 2).

These preliminary results suggest the future incorporation of the C-glycosidic pseudodisaccharide fragment 10 into larger, biologically important oligosaccharides, affording carbon bridged sialyl Lewis X derivatives.

The C-glycosides of the ulosonic acids prepared by the method of the present invention may be used as pharmaceuticals and cosmetics, such as antibacterial agent, antiviral agent, antitumor agent by attaching the C-glycosides to a known antibacterial agent, antiviral agent or antitumor agent, since the C-glycosides are nonhydrolyzable in cells.

EXAMPLES

The invention will now be described more concretely by way of examples thereof. It should be noted that the examples are presented for the illustration purpose only and should not be interpreted in any restrictive way.

General methods. N-Acetylneuraminic acid was purchased (Snow Brand Milk Products Company Ltd., Tokyo, Japan). All other reagents and solvents were of reagent grade and were dried using standard procedures. Optical rotations were measured with a Perkin Elmer 141 polarimeter at 22° C. $^1$H NMR spectra were recorded at 25° C. on a Varian Unity 500 MHz spectrometer and chemical shifts are given in ppm from tetramethylsilane as internal standard. All reactions were monitored by thin layer chromatography on aluminum sheets, silica gel 60 F$_{254}$ (Merck); detection under short wavelength UV light (254 nm) and by dipping the plates into staining solution (1.0 g ceric ammonium sulfate and 24.0 g ammonium molybdate in 31 mL sulfuric acid 470 mL water) then heating. Flash chromatography was performed using 230–400 mesh silica gel 60 (Aldrich).

Example 1

Synthesis of [Methyl(5-acetamido-4,7,8,9-tetra-O-acetyl-3,5-dideoxy-α-D-glycero-D-galacto-2-nonulopyranosyl)onate]2-pyridyl Sulfone (8)

A solution of commercially available N-acetylneuraminic acid (6.0 g, 19.5 mmol) in 150 ml methanol containing 6 g of Amberlite IR-120 (H$^+$) was stirred overnight at room temperature. After filtration of the resin, the clear solution was evaporated in vacuo to dryness. The white residue was cooled to 0° C. and 100 ml acetyl chloride was added. To this cooled mixture 10 ml methanol in 15 ml acetic acid was added dropwise. After sealing, the reaction mixture was stirred for 3 days at room temp. Evaporation to dryness and co-evaporation a few times with dry toluene afforded methyl (5-acetamido-4,7,8,9-tetra-O-acetyl-3,5-dideoxy-D-glycero-β-D-galaco-2-nonulopyranosylchloride)onate, which was used without further purification. A solution of 3.54 g (6.96 mmol) of this compound and tetrabutylammonium hydrogen sulfate (2.4 g) was prepared in ethyl acetate (40 ml). Sodium carbonate (1M, 40 ml) and 2-mercaptepyridine (1.1 g, 10 mmol) were added and the reaction mixture was stirred vigorously at room temperature for 1.5 h. Ethyl acetate (50 ml) was added and the organic phase after separation was evaporated in vacuo and purified by silica gel column chromatography using ethyl acetate/petroleum ether=7/3, to obtain 3.30 g pure 2-pyridyl(methyl 5-acetamide4,7,8,9-tetra-O-acetyl-3,5-dideoxy-2-thio-D-glycero-α-D-galacto-2-nonulopyranosid)onate (85% yield).

A catalytic amount of ruthenium trichloride hydrate (~3 mg) was added to a vigorously stirred biphasic solution of methyl(2-pyridyl 5-acetamido-4,7,8,9-tetra-O-acetyl-3,5-dideoxy-2-thio-α-D-glycero-D-galacto-2-nonulopyranosid)onate (292 mg, 0.5 mmol) and sodium metaperiodate (430 mg, 2 mmol) in carbon tetrachloride (2 mL), acetonitrile (2 mL), and water (3 mL). After 5 min at room temperature, the yellow mixture was diluted and dichloromethane (100 mL), washed with water (20 mL), dried (MgSO$_4$), and concentrated. The residue was eluted from a column of silica gel with ehyl acetate to give [methyl(5-acetamido-4,7,8,9-tetra-O-acetyl-3,5-dideoxy-α-D-glycero-D-galacto-2-nonulopyranosyl)onate]2-pyridyl sulfone.

Example 2

Synthesis of Methyl 2,4,6-tri-O-benzyl-3-deoxy-3-C-(formyl)-α-D-galactopyranoside (9)

A solution of the commercially available glycoside methyl 2,4,6-tri-O-bezyl-α-D-galactopyranoside (7.92 g, 17.06 mmol) in DMSO (50 ml) and acetic anhydride (40 ml) was stirred at room temp. for 12 h. The solvent was evaporated at 10$^{-2}$ Torr and the residue was purified by flash chromatography with petroleum ether/ethyl acetate (3:1) to yield 7.25 g (92%) of methyl 2,4,6-tri-O-benzyl-α-D-xylo-hex-3-ulopyranoside as a colorless oil.—TLC [petroleum ether/ethyl acetate (3:1)]: R$_f$=0.40.

Tebbe's reagent (30 ml) of 0.5 M solution in toluene was added dropwise within 30 min to a solution of methyl 2,4,6-tri-O-benzyl-3-deoxy-3-C-(methylene)-α-D-xylo-hex-3-ulopyranoside (6.33 g, 13.69 mmol) in dry THF at 40° C. under nitrogen. Within 1 h the reaction mixture was warmed up to 0° C. and stirred for 1 h at 0° C. Then a 10% aqueous sodium hydroxide solution (15 ml) was added with vigorous stirring. After stirring for 30 min, the mixture was filtered through Celite. The organic extracts were concentrated and the residue, an orange syrup, was purified by flash chromatography with petroleum ether/ethyl acetate (3:1) to yield 5.8 g (92%) of methyl 2,4,6-tri-O-benzyl-3-deoxy-3-C-(methylene)-α-D-xylo-hex-3-ulopyransoide as a colorless oil.—TLC (petroleum ether/ethyl acetate, 3:1): $R_f$=0.54.

A solution of methyl 2,4,6-tri-O-benzyl-3-deoxy-3-C-(methylene)-α-D-xylo-hex-3-ulopyransoide (202 mg, 0.4 mmol) in dry THF (10 ml) was heated with a 9-BBN solution in THF (0.5 M, 5 ml) and then heated to reflux for 4 h. After cooling to 0° C. a 10% aqueous sodium hydroxide solution (r ml) was added within 10 min, followed by a 30% aqueous hydrogen peroxide solution (4 ml). Then stirring was continued for 30 min. The reaction mixture was extracted several times with diethyl ether, and the combined ethereal extracts were washed with a 20% aqueous sodium hydrogen sulfite solution and then with a satd. sodium chloride solution. The organic layer was dried with $MgSO_4$, concentrated to dryness and teh residue purified by flash chromatography with petroleum ether/ethyl acetate (1:1) to yield 192 mg (91%) of methyl 2,4,6-tri-O-benzyl-3-deoxy-3-C-(hydroxymethyl)-α-D-galacto-hexopyranoside as a colorless oil.—TLC (petroleum ether/ethyl acetate, 3:1): $R_f$=0.55.

To a solution of methyl 2,4,6-tri-O-benzyl-3-deoxy-3-C-(hydroxymethyl)-α-D-galacto-hexopyranoside (5.13 g, 10.72 mmol) in 25 ml of dry DMSO, 5.0 g of DCC and 0.5 ml $H_3PO4$ were added. The mixture was stirred overnight at room temperature. The reaction mixture was treated with water (100 ml), and extracted several times with ethyl acetate. The combined organic extracts were washed with a saturated sodium hydrogen carbonate solution, dried with $MgSO_4$ and concentrated in vacua. Purification of the crude product by flash chromatography with petroleum ether/ethyl acetate (4:1) gave 4.9 g (94%) methyl 2,4,6-tri-O-benzyl-3-deoxy-3-C-(formyl)-α-D-galacto-hexopyranoside as a colorless oil. —TLC (petroleum ether/ethyl acetate, 4:1): $R_f$=0.36.

Example 3

Synthesis of Methyl 5-acetamido-4,7,8,9-tetra-O-acetyl-2,6-anhydro-3,5-dideoxy-2-C-{(S)-hydroxy-[3-(methyl 2,4,6-tri-O-benzyl- 3-deoxy-α-D-galactopyranosidyl)]-methyl}-D-erythro-L-manno-nononate (10)

To a vigorously stirred neat mixture of 120 mg (0.2 mmol) [methyl(5-acetamido-4,7,8,9-tetra-O-acetyl-3,5-dideoxy-α-D-glycero-D-galacto-2-nonulopyranosyl)onate]2-pyridyl sulfone (8) and 165 mg (0.3 mmol) methyl 2,4,6-tri-O-benzyl-3-deoxy-3-C-(formyl)-α-D-galactopyranoside (9) under argon a 0.1M solution of freshly prepared $SmI_2$ in THF (7 mL, 0.7 mmol) was added dropwise at 20° C. Stirring was continued for 45 min, than the reaction mixture was poured into an aqueous ammonium chloride solution and extracted twice with ethyl acetate. The combined organic layers were dried ($MgSO_4$) and concentrated in vacuo. The residue was purified by flash chromatography with light petroleum/ethyl acetate (1:3) to yield 167 mg (88%) of 10 as a colorless foam. TLC (light petroleum/ethyl acetate, 1:3): $R_f$=0.32. $[\alpha]_D^{22}$=−18 (c=1, chloroform). $^1$H-NMR: δ=1.89–2.14 (5s, 15H, 5 $COCH_3$), 2.03 (under an $COCH_3$ signal is 1H, H-3'$_{ax}$), 2.51 (dd, $J_{3'ax,3'eq}$=12.9 Hz, $J_{3'eq,4'}$=4.6 Hz, 1H, H-3'$_{eq}$), 2.79 (bd, $J_{2,3}$=6.3 Hz, $J_{3,4}$ and $J_{3,3''}$<0.5 Hz, 1H, H-3), 3.45 (s, 3H, $OCH_3$), 3.57–3.58 (m, 2H, 2 H-6), 3.87 (bs, $J_{3'',OH}$=$J_{3'',3}$<0.5 Hz, 1H, H-3″), 3.90 (dd, $J_{5',6'}$=10.7 Hz, $J_{6',7'}$=2.1 Hz, 1H, H-6'), 3.97–4.01 (m, 2H, H-2 and H-5'), 4.05 (dd, $J_{8',9'A}$=6.1 Hz, $J_{9'A,9'B}$=12.3 Hz, 1H, H-9'$_A$), 4.31 (dd, $J_{8',9'B}$=3.9 Hz, 1H, H-9'$_B$), 4.39 (m, 2H, H-5 and OH), 4.41–4.66 (m, 7H, 3 $CH_2Ph$ and H-4 at δ=4.55), 4.90 (ddd, $J_{3'ax,4'}$=$J_{4',5}$=11.6 Hz, 1H, H4'), 5.15 (bd, $J_{NH,5'}$=9.8 Hz, 1H, NH), 5.28 (dd, $J_{7',8'}$=7.7 Hz, 1H, H-7'), 5.42 (ddd, 1H, H-8'), 7.12–7.42 (m, 15H, 3 Ph). Anal. Calcd for $C_{49}H_{61}N_1O_{18}$ (952.02): C, 61.82; H, 6.46; N, 1.47. Found: C, 61.47; H, 6.53; N, 1.26.

Example 4

Synthesis of Methyl 5-acetamido-4,7,8,9-tetra-O-acetyl-2,6-anhydro-3.5-dideoxy-2-C[hydroxy-4-(tert-butylcyclohexyl)]-D-erythro-L-manno-nononate (11)

To a vigorously stirred neat mixture of 120 mg (0.2 mmol) [methyl(5-acetamido-4,7,8,9-tetra-O-acetyl-3,5-dideoxy-α-D-glycero-D-galacto-2-nonulopyranosyl)onate]2-pyridyl sulfone (8) and and 83.0 mg (0.6 mmol) 4-tert-butylcyclohexanone under argon a 0.1 M solution of freshly prepared $SmI_2$ in THF (7 mL, 0.7 mmol) was added dropwise at 20° C. Stirring was continued for 45 min, than the reaction mixture was poured into an aqueous ammonium chloride solution and extracted twice with ethyl acetate. The combined organic layers were dried ($MgSO_4$) and concentrated in vacuo. The residue was purified by flash chromatography with light petroleum/ethyl acetate (1:3) to yield 167 mg (88%) of 11 as a colorless oil. TLC (light petroleum/ethyl acetate, 1:3): $R_f$=0.6. $[\alpha]_D^{22}$=−12 (c=1, chloroform). $^1$H-NMR (skeleton protons of the carbohydrate portion): δ=1.95 (dd, 1H, H-3$_{ax}$), 2.46 (dd, 1H, H-3$_{eq}$), 3.99 (m, 2H, H-5$_a$, H-6), 4.07 (dd, 1H, H-9$_A$), 4.32 (dd, 1H, H-9$_B$), 4.76 (ddd, 1H, H-4), 5.16 (br.d, 1H, NH), 5.30 (dd, 1H, H-7), 5.42 (ddd, 1H, H-8).

Example 5

Synthesis of Methyl 5-acetamido-4,7,8,9-tetra-O-acetyl-2,6-anhydro-3,5-dideoxy-2-C-[(dimethyl)-hydroxy methyl]-D-erythro-L-manno-nononate (13)

To a vigorously stirred neat mixture of 120 mg (0.2 mmol) [methyl(5-acetamido-4,7,8,9-tetra-O-acetyl-3,5-dideoxy-α-D-glycero-D-galacto-2-nonulopyranosyl)onate]2-pyridyl sulfone (8) and 1.0 mL acetone under argon a 0.1 M solution of freshly prepared $SmI_2$ in THF (7 mL, 0.7 mmol) was added dropwise at 20° C. Stirring was continued for 45 min, than the reaction mixture was poured into an aqueous ammonium chloride solution and extracted twice with ethyl acetate. The combined organic layers were dried ($MgSO_4$) and concentrated in vacuo. The residue was purified by flash chromatography with light petroleum/ethyl acetate (1:3) to yield 92.0 mg (94%) of 13 as a colorless oil. TLC (ethyl acetate): $R_f$=0.45. $^1$H-NMR (skeleton protons of the carbohydrate portion): δ=1.93 (dd, 1H, H-3$_{ax}$), 2.50 (dd, 1H, H-3$_{eq}$) 4.01 (m, 2H, H-5, H—C), 4.05 (dd, 1H, H-9$_A$), 4.36 (dd, 1H, H-9$_B$), 4.77 (ddd, 1H, H-4), 5.15 (br.d, 1H, NH), 5.31 (dd, 1H, H-7), 5.43 (ddd, 1H, H-8).

REFERENCES AND FOOTNOTES

Current Address: Hercules Incorporated, Research Center, Wilmington, Del. 19808.

1) *Sialic Acids*; Schauer, R. Ed., Springer-Verlag: New York, 1985. *Biological Roles of Sialic Acid*; Rosenberg A., Sheagrund, C., Eds.; Plenum: New York, 1976. Sharon N. *Complex Carbohydrates*; Addison-Wesley: London, 1975. Varki, A. *Glycobiology* 1992, 2, 25–40.

(2) Sharon, N.; Lis, H. *Science* 1989, 246, 227–234. Sharon, N.; Lis, H. *Lectins*; Chapman and Hall: London, 1989.
(3) Air, G. M.; Laver, W. G. *Proteins: Structure, Function and Genetics*, 1989, 6, 341–356, and references therein.
(4) Postema M. *C-Glycoside Synthesis*; CRC Press: Boca Raton, 1995. Recent reviews: Postema, M. *Tetrahedron* 1992, 48, 8545–8599. Herscovici, J.; Antonakis K. *Studies in Natural Products Chemistry, vol.* 10; Atta-ur-Rahman Ed.; Elsevier: Amsterdam, 1992; pp 337–403.
(5) Only the trivial alkyl and hydroxymethyl C-glycosides of Neu5Ac have been synthesized: Paulsen, H.; Matschulat, P. *Liebigs Ann. Chem.* 1991, 487–495. Walliman, K.; Vasella, A. *Helv. Chim. Acta* 1991, 74, 1520–1532. Nagy, J.; Bednarski, M. *Tetrahedron Lett.* 1991, 32 3953–3956.
(6) Examples and mechanistic studies of the Barbier reaction with organo- and glycosyl samarium compounds: Namy, J.; Collin J., Bied, C.; Kagan, H. *Synlett* 1992, 733–734. Curran, D.; Fevig, T.; Jasperse, C.; Totleben, M.; *ibid* 1992, 943–961. Molander, G.; McKie, J. *J. Org. Chem.* 1991, 56, 4112–4120. de Pouilly, P.; Chénédé, A.; Mallet, J. -M.; Sinay, P. *Bull. Soc. Chim. Fr*, 1993, 130, 256–265. Mazeas, D.; Skrydstrup, T.; Beau, J. -M. *Angew. Chem. Int. Ed. Engl.* 1995, 34, 909–912. Excellent reviews on the application of SmI$_2$: Molander, G.; Harris, C. *Chem. Rev.* 1996, 96, 307–338. Molander, G. *Chem. Rev.* 1992, 92, 29–68.
(7) The corresponding 2-thiophenylglycoside was prepared using the method of: Cao, S.; Meuneir, S.; Andersson, F.; Letellier, M.; Roy, R. *Tetrahedron: Asymmetry*, 1994, 5, 2303–2312; and oxidized to a sulfone according to: Marra, A.; Sinay, P.; *Carbohydr. Res.*, 1989, 187, 35–42.
(8) A temporary acetal tether as an attractive approach for governing the stereoselectivity in the prostaglandin synthesis was published: Stork, G.; Sher, P.; Chen, H. J. *Am. Chem. Soc.*, 1986, 108, 6384–6387. Applying this idea in the carbohydrate area resulted in a number of elegant syntheses of β-O-mannosides: Stork, G.; Kim, G. *J. Am. Chem. Soc.*, 1992, 114, 1087–1088. Stork, G.; La Clair, J. *J. Chem. Soc.*, 1996, 118, 247–248. Barresi, F.; Hindsgaul, O. *J. Am. Chem. Soc.* 1991, 113, 9376–9377. Barresi, F.; Hindsgaul, O. *Can. J. Chem.* 1994, 72, 1447–1465. Ito, Y.; Ogawa, T. *Angew. Chem. Int. Ed. Engl.* 1994, 33, 1765–1967. Dan, A.; Ito, Y.; Ogawa, T. *J. Org. Chem.* 1995, 60, 4680–4681. Exploiting a similar intramolecular aglycon delivery strategy through silicon tethers, initial examples of C-glycoside construction were proposed: Stork, G.; Suh, H.; Kim, G.; *J. Am. Chem. Soc.* 1991, 113, 7054–7066. Xin, Y. C.; Mallet, J. -M.; Sinay, P. *J. Chem. Soc. Chem. Commun.* 1993, 864. Vauzeilles, B.; Cravo, D.; Mallet, J. -M. Sinay, P. *Syntett* 1993, 522; Chénédé, A., Perrin, E.; Rekaï, E.; Sinay, P. *Synlett* 1994, 420. Mazeas, D.; Skrydstrup, T.; Doumeix, O.; Beau, J. -M. *Angew. Chem. Int. Ed. Engl.* 1994, 33, 1383–1386. Mallet, A.; Mallet, J. -M.; Sinay, P. *Tetrahedron: Asymmetry* 1994, 5, 2593–2608.
(9) $^1$H-NMR data of 7 match published: Schmid, W.; Christian, R.; Zbiral, E. *Tetrahedron Lett.*, 1988, 29, 3643–3646.
(10) Schmidt, R.; Beyerbach, A. *Liebigs Ann. Chem.* 1992, 983–986.
(11) Girard, P.; Namy, J.; Kagan, H. *J. Am. Chem. Soc.* 1980, 102, 2693–2698.
(12) Kanie, O.; Kiso, M.; Hasegawa, A. *J. Carbohydr. Chem.* 1988 7, 501–506.
(13) Ahn, N.; Bisenstein, O. *Nouv. J. Chim.* 1977, 1, 61–70.
(14) Bürgi, H.; Dunitz, J.; Shefter, E. *J. Am. Chem. Soc.* 1973, 95, 5065–5067.

What is claimed is:

1. A method for synthesizing C-glycosides of ulosonic acids comprising the step of reacting an ulosonic acid sulfone or phosphite with an aldehyde or ketone compound in the presence of a lanthanide metal halide.

2. The method according to claim 1, wherein said lanthanide metal halide is a halide of samarium (II).

3. The method according to claim 2, wherein said halide is SmI$_2$.

4. The method according to claim 1, wherein said aldehyde or ketone is represented by formula (II):

(II)

wherein R$^4$ is any group which does not hinder the reaction; R$^5$ independently is any group which does not hinder the reaction; R$^6$ is hydrogen, an alkyl group or an aryl group; X is oxygen, alkylamine, arylamine, methylene or substituted methylene; n is an integer of 0 or 1.

5. The method according to claim 1, wherein the c-glycosides contain a quaternary carbon.

6. A method for synthesizing C-glycosides of neuraminic acids or sialic acids comprising the step of reacting a protected neuraminic acid or sialic acid sulfone or phosphite with an aldehyde or ketone compound in the presence of a lanthanide metal halide.

7. The method according to claim 6, wherein said protected neuraminic acid or sialic acid sulfone or phosphite are represented by formula (I):

(I)

wherein R$^1$ is an aryl sulfone, heteroaromatic sulfone or dialkyl phosphite group; R$^2$ independently is any group or atom which does not hinder the reaction; R$^3$ is any group or atom which does not hinder the reaction; and X is oxygen, alkylamine, arylamine, methylene or substituted methylene.

8. The method according to claim 6, wherein said protected neuraminic acid or sialic acid sulfone or phosphite are represented by any one of the following formulae:

wherein $R^1$, $R^2$, $R^3$ and X have the same meanings as in Formula (I).

9. The method according to claim 6, wherein the c-glycosides contain a quaternary carbon.

10. A method for synthesizing C-glycosides of 3-deoxy-D-mannooctulosonic acid comprising the step of reacting a protected 3-deoxy-D-mannooctulosonic acid sulfone or phosphite with an aldehyde or ketone compound in the presence of a lanthanide metal halide.

11. The method according to claim 10, wherein the c-glycosides contain a quaternary carbon.

12. The method according to claim 1, 3, 4, 6, 7 or 8, wherein said aldehyde or ketone is represented by any one of the following formulae:

wherein $R^3$, $R^4$, $R^5$ and X have the same meanings as in Formula (I) and Formula (II).

13. A samarium III adduct of an ulosonic acid.

14. The samarium III adduct according to claim 13, wherein said samarium III is attached to a quaternary carbon atom.

15. A samarium adduct of an neuraminic acid or a sialic acid.

16. The samarium III adduct according to claim 15, wherein said samarium III is attached to a quaternary anomeric carbon atom.

17. A samarium III adduct of 3-deoxy-D-mannooctulosonic acid.

* * * * *